United States Patent
Fukasawa et al.

(10) Patent No.: US 10,005,078 B2
(45) Date of Patent: Jun. 26, 2018

(54) FUEL SYNTHESIS CATALYST AND FUEL SYNTHESIS SYSTEM

(71) Applicant: Kabushiki Kaisha Toshiba, Minato-ku (JP)

(72) Inventors: Takayuki Fukasawa, Yokohama (JP); Kenji Essaki, Kawasaki (JP); Shinsuke Matsuno, Minato (JP); Takashi Kuboki, Ota (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 0 days. days.

(21) Appl. No.: 15/255,741

(22) Filed: Sep. 2, 2016

(65) Prior Publication Data
US 2017/0267932 A1   Sep. 21, 2017

(30) Foreign Application Priority Data
Mar. 16, 2016 (JP) .................. 2016-053111

(51) Int. Cl.
*B01J 35/02* (2006.01)
*B01J 23/83* (2006.01)
(Continued)

(52) U.S. Cl.
CPC .......... *B01J 35/026* (2013.01); *B01J 23/755* (2013.01); *B01J 23/83* (2013.01); *B01J 35/0013* (2013.01);
(Continued)

(58) Field of Classification Search
CPC . C10G 2/50; C10G 2/332; C10G 2/341; B01J 35/008; B01J 35/023; B01J 35/0013; B01J 35/026; C07C 1/0435
See application file for complete search history.

(56) References Cited

U.S. PATENT DOCUMENTS

| 4,032,556 A | 6/1977 | Banks |
| 4,242,103 A | 12/1980 | Rabo et al. |
| 2017/0001168 A1* | 1/2017 | Park ................ B01J 20/28 |

FOREIGN PATENT DOCUMENTS

| EP | 0 225 953 A1 | 6/1987 |
| JP | 62-140652 | 6/1987 |

(Continued)

OTHER PUBLICATIONS

Shohei Tada et al. "Ni/CeO$_2$ catalysts with high Co$_2$ methanation activity and high CH$_4$ selectivity at low temperatures", International Journal of Hydrogen Energy 37, 2012, 5 pages.

*Primary Examiner* — Lessanework Seifu
(74) *Attorney, Agent, or Firm* — Oblon, McClelland, Maier & Neustadt, L.L.P.

(57) ABSTRACT

A fuel synthesis catalyst of an embodiment for hydrogenating a gas includes at least one selected from the group consisting of; carbon dioxide and carbon monoxide, the catalyst comprising, an oxide base material containing at least one oxide selected from the group consisting of; Al$_2$O$_3$, MgO, TiO$_2$, and SiO$_2$, first metal particles containing at least one metal selected from the group consisting of; Ni, Co, Fe, and Cu and brought into contact with the oxide base material, and a porous oxide layer containing at least one selected from the group consisting of; CeO$_2$, ZrO$_2$, TiO$_2$, and SiO$_2$ and having an interface with each of the first metal particles and the oxide base material.

16 Claims, 8 Drawing Sheets

(51) Int. Cl.
*C07C 29/156* (2006.01)
*C10G 2/00* (2006.01)
*B01J 23/755* (2006.01)
*B01J 35/00* (2006.01)
*C10L 1/02* (2006.01)
*C10L 1/04* (2006.01)

(52) U.S. Cl.
CPC ........... *B01J 35/023* (2013.01); *C07C 29/156* (2013.01); *C10G 2/332* (2013.01); *C10G 2/341* (2013.01); *C10L 1/02* (2013.01); *C10L 1/04* (2013.01); *C10L 2200/0492* (2013.01); *C10L 2290/42* (2013.01)

(56) References Cited

FOREIGN PATENT DOCUMENTS

| | | |
|---|---|---|
| JP | 63-24979 | 5/1988 |
| JP | 2009-34650 | 2/2009 |
| JP | 2010-44966 | 2/2010 |
| JP | 2012-187485 | 10/2012 |
| JP | 5094028 | 12/2012 |

\* cited by examiner

FUEL SYNTHESIS CATALYST AND FUEL SYNTHESIS SYSTEM

CROSS-REFERENCE TO RELATED APPLICATION

This application is based upon and claims the benefit of priority from Japanese Patent Application No. 2016-53111, filed on Mar. 16, 2016; the entire contents of which are incorporated herein by reference.

FIELD

Embodiments described herein relate generally to a fuel synthesis catalyst and a fuel synthesis system.

BACKGROUND

In recent years, renewable energy of sunlight, wind power, or the like has attracted attention as safe and clean energy, and an increase in introduction quantity thereof is expected in the future. However, such renewable energy has a low operation rate and a large output fluctuation in a short time, and has a problem in terms of stable supply. Further, if a large quantity of such renewable energy is introduced, a problem arises in that the introduced energy is not completely consumed and remains as surplus power. In this regard, there is a demand for development of techniques of storing electric power such that electric power can be stably supplied and only a necessary amount of electric power can be supplied whenever it is needed even if the introduction of such renewable energy increases. For storing electric power, in addition to a method of storing electric power in the form of electricity, a method of converting electric power into chemical energy and storing the chemical energy has been investigated. In particular, the method of storing electric power in the form of chemical energy has advantages in that the chemical power can be stored in the unit of several days to weeks or a longer span and the chemical power can be transported and used at a different place as necessary. Recently, a method of storing the electric power in the form of hydrogen attracts attention; however, methane or methanol, which is excellent in volumetric energy density as compared with hydrogen, is also a major candidate. In particular, regarding methane or the like, there are a plenty of devices capable of directly using methane or the like as a fuel and the infrastructure therefor is also established.

For example, reaction (1) in which methane is synthesized from hydrogen ($H_2$) obtainable by electrolyzing water by renewable energy and carbon dioxide ($CO_2$) and reaction (2) in which methanol is synthesized from hydrogen ($H_2$) and carbon monoxide (CO) are mentioned.

$$CO_2 + 4H_2 \rightarrow CH_4 + 2H_2O \quad (1)$$

$$CO + 2H_2 \rightarrow CH_3OH \quad (2)$$

This reaction (1) called Sabatier reaction is a reaction for reductive regeneration of $CO_2$ that is one of causes of global warming, and since the reaction is performed at a relatively low temperature of about 400° C., a great deal of research has hitherto been conducted on this reaction.

According to this reaction, the conversion of $CO_2$ and the yield of methane can be increased as the reaction approaches equilibrium and a lower temperature region; however, the reaction rate is decreased, and thus, it is more difficult to put this reaction into practical use. For this reason, when the reaction is carried out at low temperature, a noble metal-based catalyst is necessary. However, the noble metal-based catalyst is expensive. Meanwhile, when the temperature is increased to about 400° C., the reaction rate is increased and a Ni-based catalyst can be used. However, in this case, a by-product such as CO is also generated, and as a result, energy is consumed for separation of the by-product, or the like. In this regard, there is a demand for development of a non-noble metal-based catalyst having high activity at a lower temperature region and high methane yield.

As a catalyst having high activity at low temperature of the related art, for example, a Ni-based catalyst having $ZrO_2$ or $CeO_2$ as a base material has been known. It is known that a Ni catalyst supported on a $CeO_2$ base material has high reaction activity at low temperature. It is considered that these base materials have oxygen defects and help CO or $CO_2$ to be easily dissociated at lower temperature and cause the reaction with hydrogen at low temperature to be performed effectively.

However, these catalysts have metal particles supported on an oxide base material that is powder and thus are difficult to handle without any change, and it is necessary to granulate these catalysts in a suitable size using a binder or the like. Further, there is also a problem in durability such as weak binding force between the metal particles and the oxide base material. In particular, since methanation reaction is exothermic reaction, heat resistance to withstand a local temperature increase is also required.

DETAILED DESCRIPTION

A fuel synthesis catalyst of an embodiment for hydrogenating a gas includes at least one selected from the group consisting of; carbon dioxide and carbon monoxide, the catalyst comprising, an oxide base material containing at least one oxide selected from the group consisting of; $Al_2O_3$, MgO, $TiO_2$, and $SiO_2$, first metal particles containing at least one metal selected from the group consisting of; Ni, Co, Fe, and Cu and brought into contact with the oxide base material, and a porous oxide layer containing at least one selected from the group consisting of; $CeO_2$, $ZrO_2$, $TiO_2$, and $SiO_2$ and having an interface with each of the first metal particles and the oxide base material.

Hereinafter, embodiments will be described using methanation reaction of $CO_2$ as an example with reference to drawings.

As a result of intensive studies on a catalyst for synthesizing one or both of hydrocarbon fuel and alcohol fuel at low temperature from CO or $CO_2$ and $H_2$, it was found that when a composite material prepared by precipitating metal particles from the inner portion of ceramic has a structure in which an oxide capable of dissociating CO or $CO_2$ at low temperature is present to have a large contact area, a catalyst having high low-temperature activity and high reliability can be provided. In addition, it was found that when fine particles having at least one selected from the group consisting of; Fe and Co are contained in the oxide, the activity at low temperature can be further increased. Fuel synthesis catalysts of embodiments are catalysts for synthesizing hydrocarbon fuel and alcohol fuel. Therefore, in the embodiments, in terms of the configurations of the catalysts, there is no difference between a hydrocarbon fuel synthesis catalyst and an alcohol fuel synthesis catalyst. A fuel to be generated varies depending on the difference in conditions of reaction using a catalyst, for example, a difference in raw material between carbon monoxide and carbon dioxide. A fuel containing one or both of hydrocarbon fuel and alcohol fuel is synthesized by the catalysts of the embodiments.

First Embodiment

A catalyst according to a first embodiment includes an oxide base material containing at least one selected from the group consisting of; $Al_2O_3$, $MgO$, $TiO_2$, and $SiO_2$, first metal particles supported on the oxide base material and containing at least one metal selected from the group consisting of; Ni, Co, Fe, and Cu, and a porous oxide layer brought into contact with each of the first metal particles and the oxide base material to have interfaces therewith and containing at least one selected from the group consisting of; $CeO_2$, $ZrO_2$, $TiO_2$, and $SiO_2$. Such a catalyst is a fuel synthesis catalyst for hydrogenating a gas containing carbon dioxide and/or carbon monoxide.

Figure 1A:
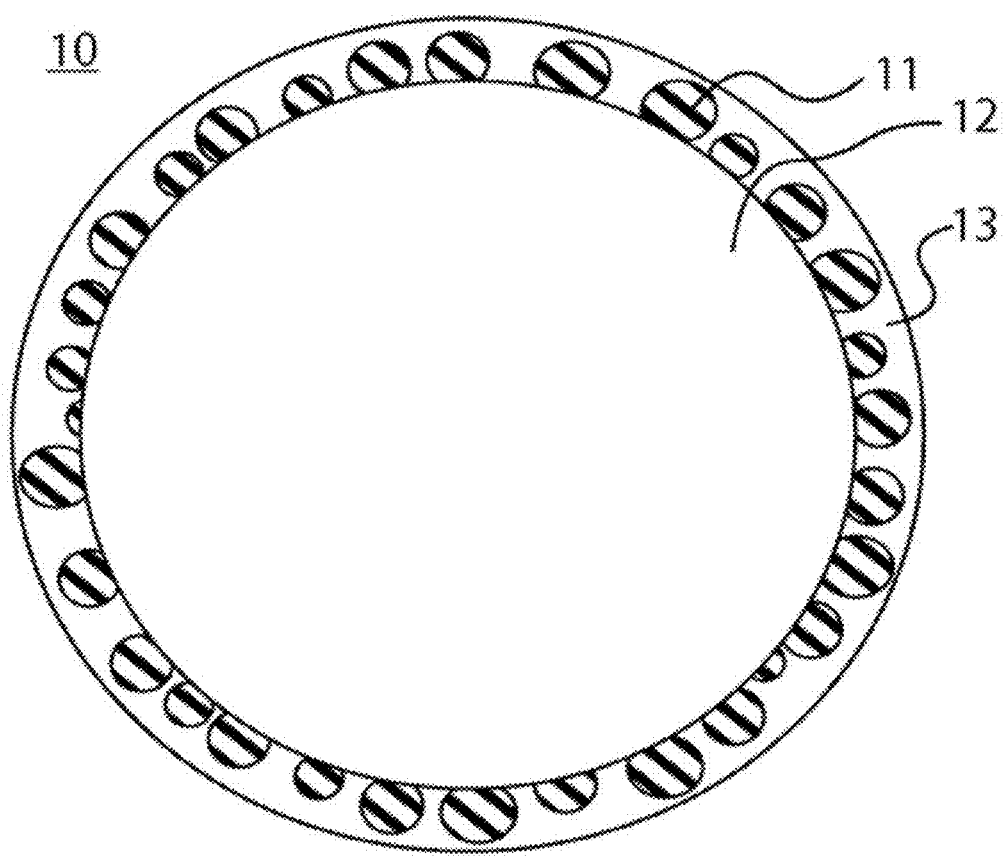
FIG. 1A is a schematic diagram of the cross-sectional structure of a catalyst according to an embodiment.
Figure 1B:
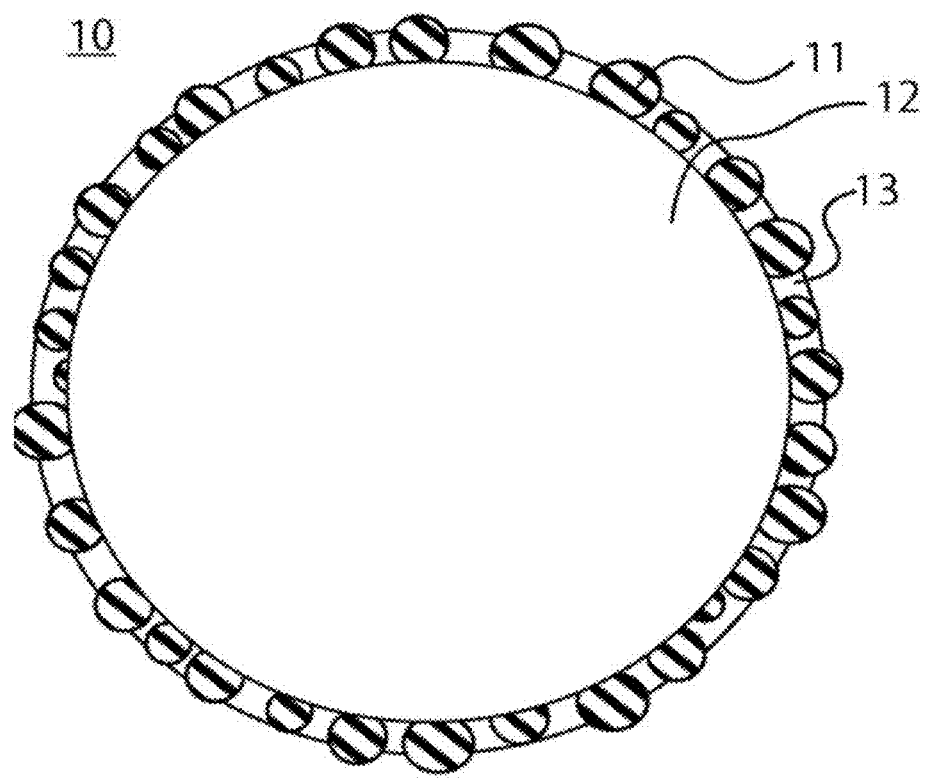
FIG. 1B is a schematic diagram of the cross-sectional structure of the catalyst according to the embodiment.
Figure 1C:
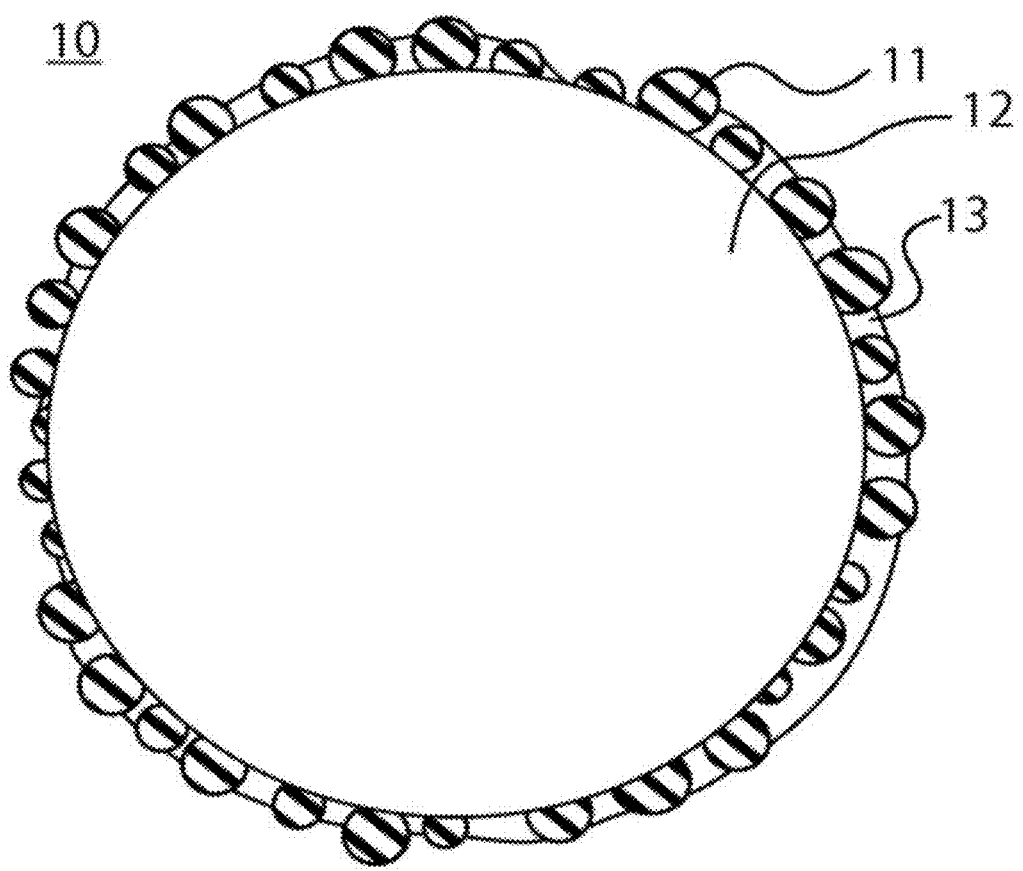
FIG. 1C is a schematic diagram of the cross-sectional structure of the catalyst according to the embodiment.

FIG. 1A, FIG. 1B, and FIG. 1C illustrate schematic diagrams of the cross-sectional structure of a catalyst material according to an embodiment.

A catalyst 10 according to the embodiment includes metal particles 11, an oxide base material 12, and an oxide layer 13. The catalyst 10 according to the embodiment is preferably a catalyst formed by the metal particles 11, the oxide base material 12, and the oxide layer 13.

In the catalyst 10 of the first embodiment, the first metal particles 11 are brought into contact with the oxide base material 12. The oxide layer 13 has an interface with the first metal particles 11. The oxide layer 13 has an interface with the oxide base material 12. Further, it is preferable that the oxide layer 13 partially or entirely cover the oxide base material 12 with which the first metal particles 11 are brought into contact. A configuration in which the first metal particles 11 are bonded to the oxide base material 12 to be physically brought into surface contact with the oxide base material 12 is preferable.

There are differences between the catalyst 10 of FIG. 1A and the catalyst 10 of FIG. 1B. The oxide layer 13 of FIG. 1A covers the first metal particles 11 and the oxide base material 12; in contrast, the oxide layer 13 of FIG. 1B partially covers the first metal particles 11 and the oxide base material 12 and at least some of the first metal particles 11 are exposed. In FIG. 1B, the first metal particles 11 and the oxide base material 12 covered with the oxide layer 13 are included. The ratio of coverage and partial coverage with the oxide layer 13 can be set to an arbitrary ratio. In the catalyst 10 of FIG. 1C, the oxide layer 13 partially covers the oxide base material 12 with which the first metal particles 11 are brought into contact. The catalyst 10 of FIG. 1C is different from the catalysts 10 of FIG. 1A and FIG. 1B in that some of the first metal particles 11 are not brought into contact with the oxide layer 13 and some of surfaces, which the first metal particles 11 are not brought into contact with, of the oxide base material 12 are not covered with the oxide layer 13. In addition, a combination of cross-sectional forms of FIG. 1A, FIG. 1B, and FIG. 1C may be employed as the catalyst 10 of the embodiment. Incidentally, as a modified example of FIG. 1C, a form in which some of the first metal particles 11 are not brought into contact with the oxide layer 13 but surfaces, which the first metal particles 11 are not brought contact with, of the oxide base material 12 are covered with the oxide layer 13 and a form in which some of surfaces, which the first metal particles 11 are not brought into contact with, of the oxide base material 12 are not covered with the oxide layer 13 but the first metal particles 11 are brought into contact with the oxide layer 13 are mentioned.

As illustrated in FIG. 1A, in the cross-section, in a case where the oxide layer 13 entirely covers the oxide base material 12 with which the first metal particles 11 are brought into contact, the oxide base material 12 is covered with the first metal particles 11 and the oxide layer 13, the first metal particles 11 have an interface between the first metal particle 11 and the oxide base material 12 and an interface between the first metal particle 11 and the oxide layer 13, and have no exposed surface.

As illustrated in FIG. 1B, in the cross-section, in a case where the oxide layer 13 covers the oxide base material 12 with which the first metal particles 11 are brought into contact and at least some of the first metal particles 11 are exposed, the oxide base material 12 is covered with the first metal particles 11 and the oxide layer 13, and the first metal particles 11 have exposed surfaces, an interface between the first metal particle 11 and the oxide base material 12, and an interface between the first metal particle 11 and the oxide layer 13.

As illustrated in FIG. 1C, in the cross-section, in a case where the oxide layer 13 partially covers the oxide base material 12 with which the first metal particles 11 are brought into contact, some of the first metal particles 11 are not brought into contact with the oxide layer 13, and some of surfaces, which the first metal particles 11 are not brought into contact with, of the oxide base material 12 are not covered with the oxide layer 13, the oxide base material 12 is partially covered with the first metal particles 11 and the oxide layer 13, and the first metal particles 11 have exposed surfaces, an interface between the first metal particle 11 and the oxide base material 12, and an interface between the first metal particle 11 and the oxide layer 13. Some of the first metal particles 11 have an interface with the oxide base material 12 but do not have an interface with the oxide layer 13.

The particle diameter of the catalyst 10 is preferably 2 mm or more and 10 mm or less. When the particle diameter of the catalyst 10 is less than 2 mm, in a case where a reaction tube is filled with the catalyst, pressure loss increases, which is not favorable. In addition, when the particle diameter of the catalyst 10 is more than 10 mm, the first metal particles existing deeply inside the catalyst are not utilized, and thus useless portions increase, which is not favorable. Regarding the particle diameter of the catalyst 10, the catalyst 10 is subjected to slice processing and the processed sample is observed with an optical microscope. 50 particles having the clearest outline of the catalyst in the photographed image are selected, a circumscribed circle diameter $\phi A1$ and an inscribed circle diameter $\phi A2$ of each of 50 particles are obtained, and a value obtained from $(\phi A1+\phi A2)/2$ is designated as the particle diameter of each particle. Then, an average value of particle diameters of 40 particles, excluding five particles having the obtained maximum particle diameter and five particles having the obtained minimum particle diameter, is designated as the average particle diameter of the catalyst 10.

The first metal particles 11 are particles containing at least one element selected from the group consisting of; Ni, Co, Fe, and Cu. It is preferable that the first metal particles 11 exist to be interposed between the oxide base material 12 and the oxide layer 13. The first metal particles 11 may exist inside of the oxide base material 13. These first metal particles are preferably any one of metal particles formed by a single element, metal particles in which a plurality of particles formed by a single element are mixed, alloy particles containing a plurality of elements, and particles in which metal particles and alloy particles are mixed. The first metal particles 11 are more preferably particles containing at least Ni particles. The first metal particles 11 are more preferably particles formed by at least one element selected from the group consisting of; Ni, Co, Fe, and Cu, from the viewpoint of obtaining a catalyst which is inexpensive and excellent in low-temperature activity.

The particle diameter of the first metal particle 11 is preferably in a range of from 2 nm to 200 nm. The reason for this is that particles having a particle diameter of less than 2 nm may less distribute to reaction, and when the particle diameter is more than 200 nm, the specific area of the catalyst may be decreased and adjacent particles are easily aggregated while in use. The range is more preferably 10 nm or more and 150 nm or less in terms of the average particle diameter.

Herein, the particle diameter of the first metal particles 11 and the average particle diameter thereof will be described. For measurement of the particle diameter of the first metal particles 11, a surface layer portion of the catalyst 10 that is an area including at least the first metal particles 11 and includes at least the surface of the oxide base material 12 is observed to obtain the particle diameter. In this case, the catalyst 10 is subjected to slice processing to have a form including the surface layer portion of the catalyst and the vicinity of the surface layer portion is observed by a TEM (Transmission Electron Microscope) with a magnification of 100,000 or more. For the photographing magnification, an appropriate magnification is selected depending on the size of the first metal particle 11. In a case where the first metal particles 11 are covered with the oxide layer 13 so that the first metal particles 11 cannot be confirmed, a sample is polished and then a surface in which the first metal particles 11 can be confirmed may be observed. Then, 50 particles having the clearest outline of the first metal particle 11 in the photographed image are selected, a circumscribed circle diameter $\phi B1$ and an inscribed circle diameter $\phi B2$ of each of 50 particles are obtained, and a value obtained from $(\phi B1+\phi B2)/2$ is designated as the particle diameter of each particle. As necessary, element specification may be performed by TEM-EDS (Transmission Electron Microscope/Energy dispersive Spectrometry). Then, an average value of particle diameters of 40 particles, excluding five particles having the obtained maximum particle diameter and five particles having the obtained minimum particle diameter, is designated as the average particle diameter of the first metal particles 11.

The oxide base material 12 is a base material containing at least one metal oxide selected from the group consisting of; $Al_2O_3$, MgO, $TiO_2$, and $SiO_2$. A plurality of these oxides may exist in a mixed state, but the oxide base material 12 is a structural body having a particulate shape with a size suitable for practical use or a honeycomb shape. The first metal particles 11 and the oxide layer 13 exist on the surface of the oxide base material 12, and the first metal particles 11 and the oxide layer 13 are brought into physical contact with the oxide base material 12. It is preferable that the oxide layer 13 exist on the surface other than the portion, in which the first metal particles 11 exist, of the surface of the oxide base material 12, but some of the surfaces of the oxide base material 12 may be exposed surfaces in which neither the first metal particles 11 nor the oxide layer 13 exists.

The oxide base material 12 is formed by a so-called metal/ceramic composite material that is an integral structure with the first metal particles 11 which is in physical contact with the surface of the oxide base material 12 or the first metal particles 11 which is in physical contact with the surface of the oxide base material 12 and exists inside of the oxide base material 12. It is preferable that the first metal particles 11 be directly bonded to (compounded with) the oxide base material 12 and each particle of the first metal particles 11 exists on the oxide base material 12 in an independently dispersed manner. It is more preferable that all of the first metal particles 11 be directly bonded to (compounded with) the oxide base material 12 and each particle of the first metal particles 11 exists on the oxide base material 12 in an independently dispersed manner. Specifically, as illustrated in FIG. 1A and FIG. 1B, at least some of the first metal particles 11 are buried in the oxide base material 12. Such a structure can be confirmed by observing the cross-sectional portion of the catalyst by a TEM with high magnification. Since the catalyst 10 is obtained by reducing a compound of an easily-reducible oxide and a hardly-reducible oxide, the catalyst 10 has a structure in which the first metal particles 11 derived from the easily-reducible oxide are precipitated on the surface portion of the base material during reduction. Therefore, a buried structure is entirely confirmed (80% or more of the total number of the first metal particles 11).

Examples of combinations of the first metal particles 11 and the oxide base material 12 include Ni—$Al_2O$, Co—$Al_2O_3$, Fe—$Al_2O_3$, NiCo—$Al_2O_3$, NiFe—$Al_2O_3$, NiCu—$Al_2O_3$, CoFe—$Al_2O_3$, Ni—MgO, Co—MgO, Fe—MgO, NiCo—MgO, NiFe—MgO, NiCu—MgO, CoFe—MgO, Ni—$TiO_2$, Co—$TiO_2$, Fe—$TiO_2$, NiCo—$TiO_2$, NiFe—$TiO_2$, NiCu—$TiO_2$, CoFe—$TiO_2$, Ni—$SiO_2$, Co—$SiO_2$, Fe—$SiO_2$, NiCo—$SiO_2$, NiFe—$SiO_2$, NiCu—$SiO_2$, and CoFe—$SiO_2$. These can be used singly or in combination.

The composite material formed by the first metal particles 11 and the oxide base material 12 preferably has a porous structure. From the viewpoint of improving the catalyst activity at low temperature, a structure having both of macro pores and micro pores is preferable. Specifically, the composite material preferably has a structure having macro pores, which have a pore diameter of 200 nm or more and 10 µm or less, enabling reaction to act on the catalyst on the deep portion of ceramic and micro pores, which have a pore diameter of 2 nm or more and 30 nm or less, for providing a large reaction area.

The composition of the oxide contained in the oxide base material 12 is obtained by X-ray diffraction (XRD) measurement.

Further, the porous oxide layer 13 containing at least one selected from the group consisting of; $CeO_2$, $ZrO_2$, $TiO_2$, and $SiO_2$ is formed on the surface portion of the base material of the metal/oxide composite material in a state where the oxide layer 13 is brought into contact with the first metal particles 11. These oxides have characteristics of easily dissociating CO or $CO_2$, which has been adsorbed once, at lower temperature and play an important role of improving the catalyst activity at low temperature. The pore diameter of the oxide layer 13 is preferably 2 nm or more and 10 μm or less.

The oxide layer 13 is formed to partially or entirely cover the composite material. The oxide layer 13 may be formed to cover the surface portions of the first metal particles 11 as illustrated in FIG. 1A or may be formed in a state where the first metal particles 11 are exposed to the surface portion as illustrated in FIG. 1B. As illustrated in FIG. 1C, a part of the oxide base material 12 may have an exposed surface or may include a portion in which some of the first metal particles 11 are not brought into contact with the oxide base material 12. A porous layer having gas diffusivity is preferably employed. The methanation reaction is considered to occur at a so-called three-phase interface in which $CO_2$ (or reduced CO) and hydrogen as reactive species and the first metal particle 11 as a catalyst are brought into contact with one another. The activity is improved by forming a large number of this three-phase interface. Such a porous structure enables gas to easily come and go and can increase this three-phase interface place. That is, $CO_2$, which has been adsorbed once by the oxide layer 13 is moved smoothly on the surface of the first metal particles 11 as a catalyst, and dissociated at low temperature, smoothly reacts with hydrogen on the surface of the first metal particle 11, or $CO_2$ is easily reduced by oxygen defect, and thus reaction until $CH_4$ is obtained can be performed without remaining CO generated in the course of the reaction. For these reasons, even when the oxide layer 13 has the same composition as the oxide base material 12, since the contact area with the first metal particle 11 is increased as illustrated in FIGS. 1A to 1C, an effect of further activating the reaction at low temperature can be expected.

Since the oxide layer 13 is porous, the three-phase interface of the first metal particle 11 exists even in a case where the first metal particle 11 has or does not have an exposed surface. Instead, since the oxide layer 13 forms an interface with the first metal particle 11, the oxide layer 13 supplying CO or $CO_2$ exists in the vicinity of the first metal particle 11 so that the reaction is promoted. Further, since generated hydrocarbon or alcohol passes through porous pores of the oxide layer 13 to be discharged to the outside of the catalyst 10, the oxide layer 13 has both functions of supplying a reaction raw material and providing a discharge passage of a product. Moreover, since the oxide layer 13 dissociates CO or $CO_2$ at low temperature, low-temperature activity of the catalyst 10 using the first metal particles 11 is improved by the presence of the oxide layer 13.

The thickness of such an oxide layer 13 is preferably at least 10 nm or more in terms of the average value. The reason for this is that with such a thickness of 10 nm or more, the oxide layer can be formed to cover some portions of the first metal particles 11 which are precipitated by reduction. A portion, which is brought into contact with the oxide base material 12, of a general catalyst is almost dot-like; on the other hand, with the above-described configuration, a ridge portion of the first metal particle 11 can contribute to reaction. The thickness of the oxide layer 13 is preferably thicker, but when the thickness is too thick, diffusion of gas is delayed, and thus the thickness is preferably within about 10 μm at most.

Whether the first metal particles 11 are present in the oxide layer 13 can be analyzed by surface observation of the catalyst 10 by a SEM or by observation of the cross-section of the structure by a TEM. For example, the surface portion of the catalyst 10 is observed by a high-resolution SEM. The composition analysis of the surface portion is performed in advance by EDS or the like, a portion where the oxide layer 13 such as $CeO_2$ exists is searched, and then the portion is enlarged to at least 10,000 times or more. Then, the acceleration voltage is changed to obtain information in the depth direction and information of the first metal particles 11, such as Ni, located under the oxide layer 13, such as $CeO_2$, can be obtained by performing photographing by a reflected electron image. The pore diameter of the oxide layer 13 can be also obtained by the above-described method. Incidentally, also in a case where the oxide base material 12 and the oxide layer 13 are formed by the same compound, the cross-section observation described above is performed, and the structure analysis may be performed from the characteristic of the interface where crystallinity (for example grain size) varies.

In addition, the oxide layer 13 may contain an oxide such as $Sm_2O_3$, $Y_2O_3$, $Sc_2O_3$, $Gd_2O_3$, CaO, or MgO. The reason for this is that when these oxides are solid-solubilized, the crystalline phase of the oxide layer 13 is stabilized, oxygen defect is formed, there is a beneficent influence on dissociation behavior of $CO_2$, and the catalyst activity at lower temperature can be improved. These oxides to be solid-solubilized are contained in 30 mol % or less with respect to the number of moles of the oxide layer 13.

The content of the first metal particles 11 in the entire catalyst 10 is preferably 5% by mass or more. When the content is less than 5% by mass, the effect as the catalyst is small. In addition, the content of the first metal particles 11 is preferably 40% by mass or less. The reason for this is that when the content is more than 40% by mass, a distance between the first metal particles 11 are decreased, the first metal particles are easily combined or aggregated while in use (a so-called sintering phenomenon easily occurs), and thus the performance thereof are deteriorated. The content of the first metal particles 11 in the entire catalyst 10 is more preferably in a range of from 5% by mass to 25% by mass. The content of the first metal particles 11 in the entire catalyst 10 is still more preferably in a range of from 9.4% by mass to 16.2% by mass. The content of the first metal particles 11 in the entire catalyst 10 is measured by inductively coupled plasma (ICP) analysis.

(Production Method)

Next, the method for producing the catalyst material according to the embodiment will be described.

In the following description, a catalyst having a size of 2 mm or more and 10 mm or less which is suitable for practical use is described as an example, and the embodiment is not limited thereto. For example, a material may be prepared using powder having a large specific area as a base material, and the material may be granulated in a size suitable for practical use by using an inorganic binder or by performing heat treatment.

First, a material that becomes the oxide base material 12 is prepared. The material can be obtained by using powder or granulated powder of $Al_2O_3$, MgO, $TiO_2$, $SiO_2$, or the like and mixed powder thereof, performing molding by adding a binder or the like, and performing heat treatment under the proper conditions. Herein, in the case of using $Al_2O_3$, $Al_2O_3$ of γ phase having a large specific area is preferably used. As the binder, an organic binder, an inorganic binder, or the like is appropriately selected depending on the powder to be used. Regarding molding, extrusion molding, a roll molding method, or the like can be used. The size of a molded body is preferably set to a size suitable for practical use, and is preferably about 2 mm or more and less than 10 mm. There is no particular limitation on the shape of the molded body, and the molded body can be molded or processed in an easily-handled shape such as a spherical shape, a cylindrical shape, a star shape, or a honeycomb shape.

Unless the molded body is molded or processed in a honeycomb shape, in the case of a pellet shape, since the volume of the inner portion, which does almost not contribute to reaction, of the catalyst 10 increases as the particle diameter of the catalyst 10 is larger than necessary, performance of the catalyst per volume is deteriorated. Therefore, the particle diameter of the catalyst 10 is preferably set to a size not exceeding 1 cm.

Next, the surface layer portion is turned into a composite oxide by using the oxide base material 12. A compound containing at least one element selected from the group consisting of; Ni, Co, Fe, and Cu is brought into contact with the porous oxide base material 12 and is subjected to heat reaction, and thus at least the surface layer portion of the oxide base material 12 is turned into a composite oxide. Examples of the compound include nitrate, sulfate, chloride salt, acetate, carbonate, and hydroxide which contain metal elements mentioned in the first metal particles 11. In order to form a composite oxide up to the inner portion of the oxide base material 12, an impregnation method using a solution technique is preferably used.

For example, a case where spherical particles formed by $\gamma$-$Al_2O_3$ is used as the oxide base material 12 and nickel nitrate hydrate is used as a metal compound will be described as an example. The $\gamma$-$Al_2O_3$ spheres are immersed in an aqueous solution of nickel nitrate, which has been dissolved in a predetermined concentration, subjected to vacuum impregnation, and dried to obtain $\gamma$-$Al_2O_3$ spheres covered with nickel nitrate. The spheres are subjected to heat treatment to thermally decompose nickel nitrate, thereby forming NiO. The method of coating NiO for reacting with $Al_2O_3$ of the oxide base material 12 is not limited thereto. Then, the formed NiO is heated from 1000° C. to 1400° C. so that the oxide base material 12 and NiO generated through thermal decomposition are reacted with each other to thereby obtain a composite base material in which a part of the oxide base material 12 is turned into a $NiAl_2O_4$ composite oxide.

The layer of this composite oxide is formed on the surface portion of the composite base material. The concentration of unreacted $Al_2O_3$ increases toward the inner portion of the base material. Since the original amount of $Al_2O$, as the oxide base material 12 is sufficiently large with respect to NiO used in coating, there is no case where NiO remains after heat treatment. The composite oxide layer varies depending on an oxide used in the oxide base material 12, and for example, in the case of the Ni-based catalyst, when the base material to be used is MgO, $Ni_xMg_{1-x}O$ (0<x<1) is formed as a main composition, when the base material to be used is $TiO_2$, $NiTiO_3$ is formed as a main composition, and when the base material to be used is $SiO_2$, $Ni_2SiO_4$ is formed as a main composition. Similarly, the same applies to other metal species, Co, Fe, and Cu.

Next, the oxide layer 13 is formed on the composite base material having the composite oxide layer prepared as described above. Examples of the forming method include a method in which the first metal particles 11 are precipitated by reduction treatment and then are covered with the oxide layer 13 and a method in which the oxide layer 13 is covered on the composite oxide layer and then the first metal particles 11 are precipitated by reduction treatment. In both methods, the first metal particles 11 are precipitated by reductive precipitation.

The former performs composite oxide reduction treatment before forming the oxide layer 13. The latter performs composite oxide reduction treatment after forming the oxide layer 13. The reduction treatment is performed at a temperature range of 600 to 1100° C. in a reducing atmosphere such as hydrogen. The reducing atmosphere is not limited thereto, and heat treatment may be performed in the presence of a carbon material and in an inert atmosphere such as Ar. In a case where the reduction temperature is lower than 600° C., precipitation of the first metal particles 11 by reduction is not sufficiently performed, and in a case where the reduction temperature is higher than 1100° C., the precipitated particles are aggregated or coarsened, which is not favorable. The proper reduction temperature varies depending on a composite oxide, and for example, in the case of $Co_2TiO_4$ or the like, the reduction temperature is preferably about 700° C. The proper temperature can be determined by performing thermogravimetric analysis on the composite oxide in a reducing atmosphere. The reduction time is properly about 1 minute to 1 hour. Through the above-described treatments, the composite oxide is reduced, the incorporated metal component becomes fine particles, the fine particles are precipitated to mostly the surface of the oxide base material 12 and partly the inner portion of the oxide base material 12, and thus the metal-ceramic composite material is obtained. At this time, the first metal particles 11 are formed on the oxide base material 12 in a state where the first metal particles 11 independently are highly dispersed.

Next, the oxide layer 13 of at least one selected from the group consisting of; $CeO_2$, $ZrO_2$, $TiO_2$, and $SiO_2$ is formed on the ceramic to which the first metal particles 11 are precipitated. This oxide layer 13 may be a single oxide or a mixture of a plurality of oxides. In addition, since $CeO_2$, $ZrO_2$, or the like stabilizes the structure as the phase and forms oxygen defect, an oxide such as $Sm_2O_3$, $Y_2O_3$, $Sc_2O_3$, $Gd_2O_3$, CaO, or MgO may be solid solution in the oxide layer 13. Such a solid-solubilized product can be produced by, for example, performing impregnation, coating, and heat calcination on an aqueous solution prepared by mixing a plurality of metal salts. It should be noted that in some aqueous solutions, a metal component such as Ni may be easily eluted. In this case, the precipitated first metal particles 11 are treated to be turned into an oxide by performing heat treatment in air, and then impregnated and covered so that a solid-solubilized product can be formed. The latter producing method is different from the former producing method only in order of treatments, and has the same treatment method as in the former producing method. Therefore, the description of the latter producing method is not provided.

Some of the oxide layer 13 and the oxide base material 12 may be reacted with each other during heat treatment. For example, $CeO_2$ as the oxide layer 13 and $Al_2O_3$ of the oxide base material 12 may be reacted with each other to form $CeAlO_3$, but this phase itself also contributes to improvement in catalyst activity.

Second Embodiment

A catalyst according to a second embodiment includes an oxide base material containing at least one oxide selected from the group consisting of; $Al_2O_3$, MgO, $TiO_2$, and $SiO_2$, first metal particles supported on the oxide base material and containing at least one metal selected from the group consisting of; Ni, Co, Fe, and Cu, a porous oxide layer brought into contact with the first metal particles and the oxide base material and containing at least one selected from the group consisting of; $CeO_2$, $ZrO_2$, $TiO_2$, and $SiO_2$, and second metal particles contained in the oxide layer. Herein, a main component of the second metal particles is preferably at least one selected from the group consisting of; Fe and Co.

Figure 2A:
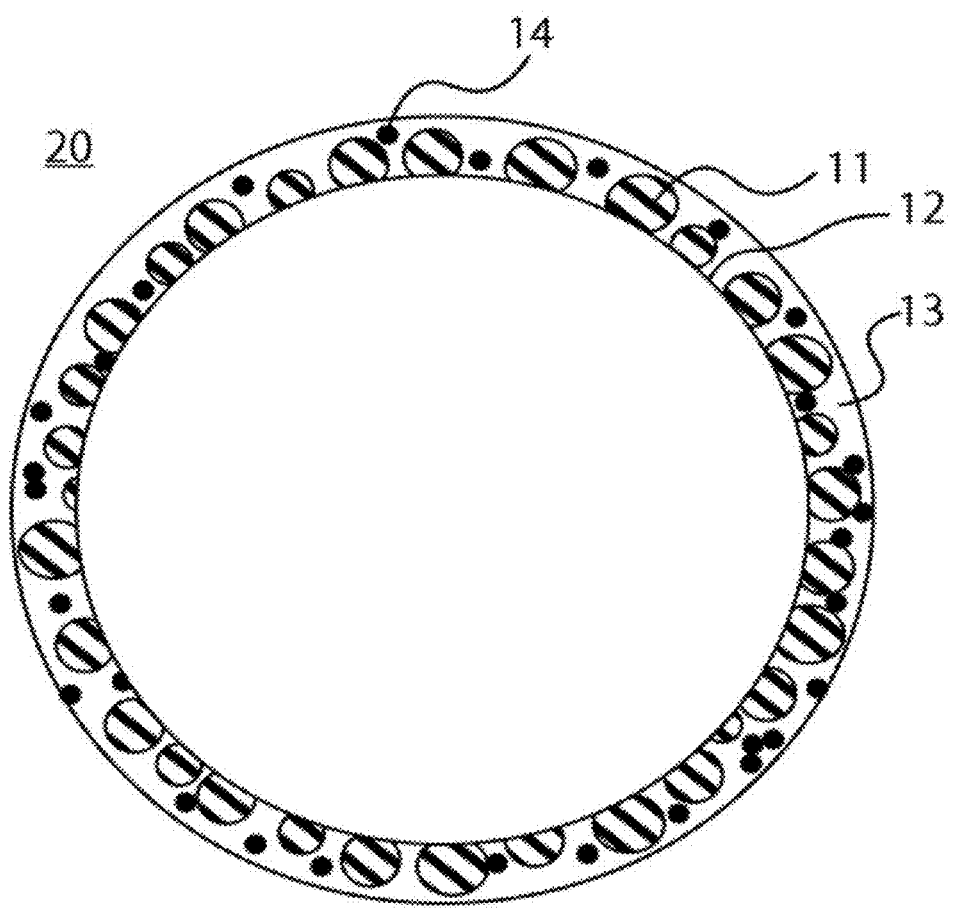
FIG. 2A is a schematic diagram of the cross-sectional structure of a catalyst according to an embodiment.
Figure 2B:
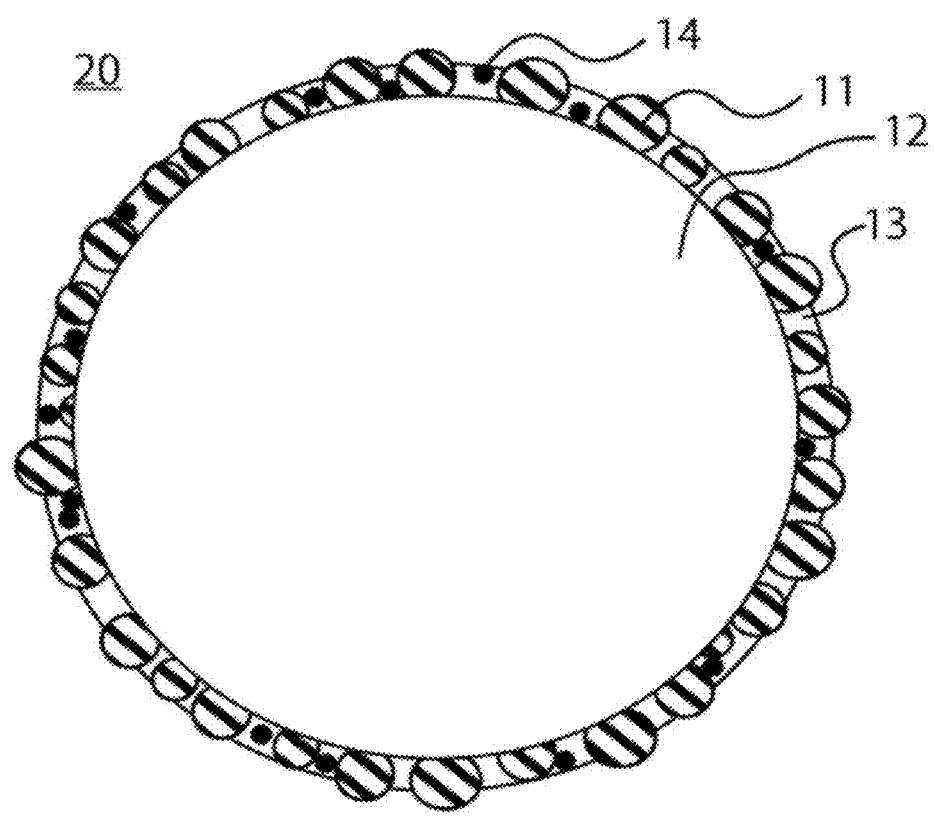
FIG. 2B is a schematic diagram of the cross-sectional structure of the catalyst according to the embodiment.
Figure 2C:
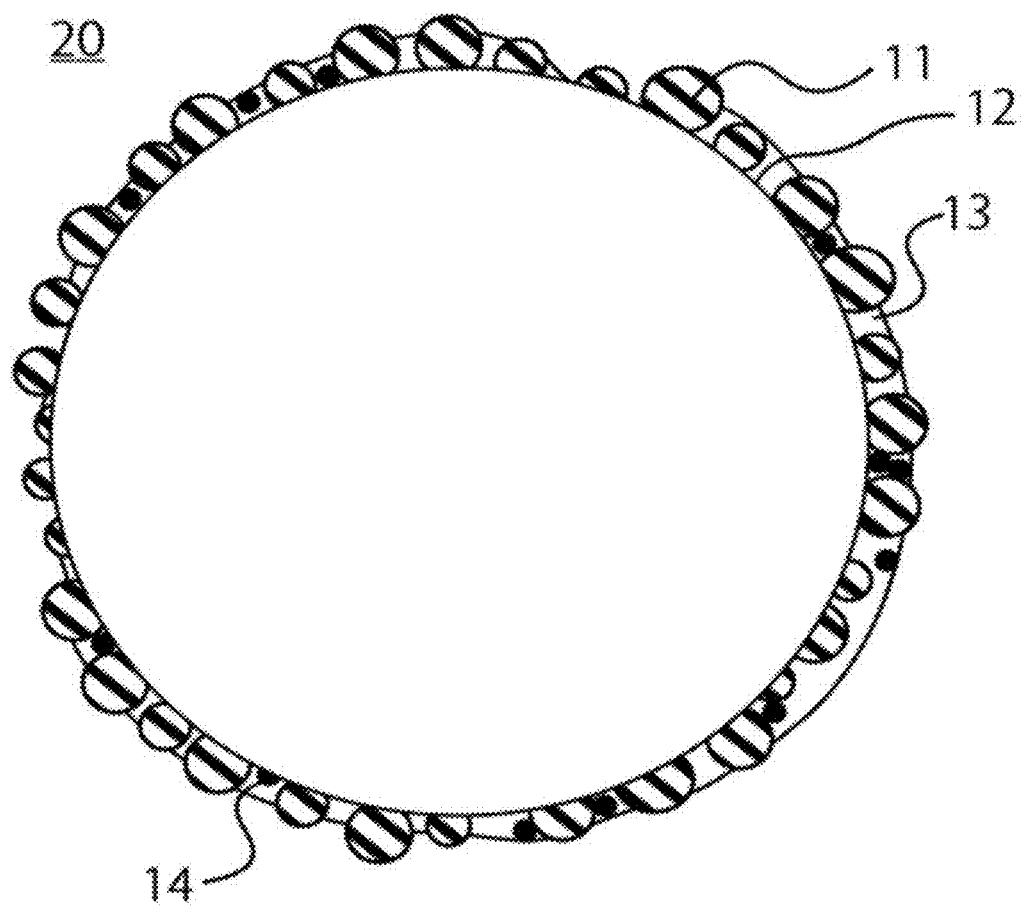
FIG. 2C is a schematic diagram of the cross-sectional structure of the catalyst according to the embodiment.

FIGS. 2A to 2C illustrate schematic diagrams of the cross-section of a catalyst 20 according to the second embodiment (FIGS. 2A to 2C illustrating two structures similarly to the first embodiment). The basic configurations of materials other than second metal particles 14 are the same as those in the first embodiment, and thus the details thereof are not provided. FIG. 2A, FIG. 2B, and FIG. 2C are different from the cross-sectional views of FIG. 1A, FIG. 1B, and FIG. 1C in that the second metal particles 14 represented as black dots are included. The characteristic of the catalyst 20 in the second embodiment is that the porous oxide layer 13 has the second metal particles 14 different from the first metal particles 11 which are formed by reductive precipitation. In FIGS. 2A to 2C, the primary particle diameter of the second metal particles 14 is smaller than the primary particle diameter of the first metal particles 11, but the magnitude relation between the particle diameters is not limited thereto.

The second metal particles 14 described herein are metal fine particles containing at least one selected from the group consisting of; Fe and Co. The size of the second metal particles 14 is preferably 1 nm or more and 200 nm or less in terms of the primary particle diameter. The particle diameter of the second metal particles 14 is obtained in the same method as in the first metal particles 11. Several particles may be aggregated to form secondary particles. The second metal particles 14 may exist in the oxide layer 13 while being brought into contact with the oxide base material 12 and the first metal particles 11 or may exist in the oxide layer 13 while being separated therefrom. In addition, the second metal particles 14 may exist on the surface portion while being brought into contact with the oxide layer 13. However, it is more preferable that the second metal particles 14 exist in the vicinity of the first metal particles 11 since the second metal particles 14 act as a cocatalyst of the first metal particles 11. When the second metal particles 14 exist in the oxide layer 13, an effect is also achieved in which the second metal particles 14 are immobilized and the aggregation of particles caused by sintering is suppressed so that durability is improved.

The second metal particles 14 exhibit higher catalyst activity particularly in a case where the second metal particles 14 are combined with Ni as the first metal particles 11. In addition, the proportion of the first metal particles 11 and the second metal particles 14 in the entire catalyst 20 is preferably 5% by mass or more and 40% by mass or less. The reason for this is as follows. When the proportion is less than 5% by mass, the effect as the catalyst 20 is small. When the proportion is more than 40% by mass, although there is no serious problem in the catalyst activity, the aggregation of metal particles occurs by sintering or the like in the case of long-term use, and thus the performance is deteriorated. From the viewpoint of efficiently utilizing the catalyst 20 without waste, the proportion is more preferably in a range of from 5% by mass to 25% by mass.

As the method for producing the catalyst 20 containing the second metal particles 14, for example, a method is mentioned in which a mixed oxide layer is formed on a composite oxide such that the oxide of the second metal particles 14 that is an easily-reducible oxide is contained in the oxide layer 13 and then reduction treatment is performed.

(Fuel Synthesis Apparatus (System))

Figure 3:
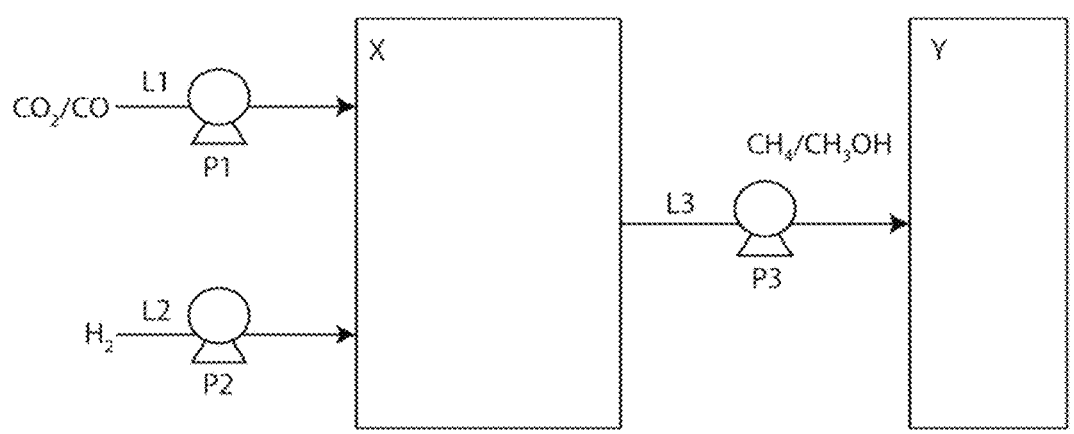
FIG. 3 is a schematic diagram of a fuel synthesis system according to an embodiment.

Next, with reference to the schematic diagram of FIG. 3, a fuel synthesis apparatus (system) using the catalyst of the embodiment will be described. The fuel synthesis apparatus includes a reaction column X provided with the fuel synthesis catalyst, a first raw material supply line L1 configured to supply one or both of carbon dioxide and carbon monoxide to the reaction column, a second raw material supply line L2 configured to supply hydrogen to the reaction column X, and a recovery unit Y configured to recovery a fuel generated by reacting one or both of the carbon dioxide and the carbon monoxide with the hydrogen using the catalyst in the reaction column X.

The reaction column X and the recovery unit Y are connected via a product supply line L3, and the fuel generated in the reaction column X moves from the reaction column X to the recovery unit Y through the product supply line L3. It is preferable that impurities in the product be removed in the recovery unit Y. The fuel generated in reaction column contains one or both of hydrocarbon fuel and alcohol fuel. In addition, although not illustrated in the drawing, the fuel synthesis apparatus is preferably configured such that unreacted carbon dioxide or carbon monoxide and hydrogen are separated from each other in the recovery unit Y and the separated components are sent to the reaction column X to be used for reaction. In addition, the recovery unit Y may further include a unit configured to consume fuel, for example, generate power using the fuel.

The temperature of reaction of the carbon dioxide or carbon monoxide with the hydrogen using the catalyst is preferably 250° C. or higher but 400° C. or lower. When the temperature is too low, the catalyst activity is lowered, which is not favorable. In addition, when the temperature is too high, deterioration of the catalyst is accelerated and energy necessary for reaction is required much more, which is not favorable. From these points of view, the temperature of reaction of the carbon dioxide or carbon monoxide with the hydrogen using the catalyst is more preferably 300° C. or higher but 350° C. or lower. At such a low temperature, a catalyst of the related art has low catalyst activity and thus is not suitable for practical use; on the other hand, the catalyst of the embodiment has excellent low-temperature activity and thus is suitable for practical use even at low-temperature conditions.

EXAMPLES

Hereinafter, specific examples will be mentioned and the effect thereof will be described. However, embodiments are not limited to these examples.

Example 1

A catalyst material was prepared under the conditions as described below.

γ-$Al_2O_3$ spherical particles having a particle diameter of 2 to 4 mm were immersed in an aqueous solution of nickel nitrate ($Ni(NO_3)_2 \cdot 6H_2O$) and subjected to impregnation treatment for 2 hours under reduced pressure in a vacuum desiccator. A sample was taken out and subjected to dry treatment, and then heat treatment was performed at 500° C. for 1 hour in air with an electrical furnace so that nickel nitrate was thermally decomposed to obtain NiO. Further, the NiO was reacted with $Al_2O_3$ of the base material by increasing the temperature to 1200° C. and performing calcination treatment for 2 hours so that some of $Al_2O_3$ of the base material became $NiAl_2O_4$ that is the composite oxide. Next, this calcined sample was subjected to reduction treatment at 1000° C. for 10 minutes in hydrogen so that first metal particles of Ni were precipitated from $NiAl_2O_4$ portion. Further, the sample subjected to reduction was immersed in an aqueous solution of cerium nitrate ($Ce(NO_3)_3 \cdot 6H_2O$) and after the resultant solution was dried, heat treatment was performed at 500° C. for 1 hour so that a $CeO_2$ layer was formed on the catalyst surface. The catalyst performance evaluation test was carried out using this sample. As a result of evaluation of the composition of this sample by ICP emission spectrometry, the content of Ni was 9.4% by mass.

(Catalyst Performance Evaluation Test)

For the test, a fixed-bed flow type reaction apparatus was used. A reaction tube having an inner diameter of 42.8 mm was charged with the catalyst mixed with $Al_2O_3$ spheres (average size of 3 mm) unrelated to the reaction, hydrogen reduction was performed at 400° C. for 1 hour, and then a gas prepared by mixing $CO_2$ and $H_2$ at a flow ratio of 1:4 was supplied at a space velocity of 6000/h. The $CO_2$ conversion and methane yield at from 250° C. to 400° C. were obtained by analyzing the outlet gas after the reaction by micro gas chromatograph. The methane yield was calculated by the following equation.

$$\text{Methane yield} = CO_2 \text{ conversion} \times \text{methane selectivity} \quad (2)$$

Further, for some samples, identification of the constituent phase by XRD and measurement of micro pore distribution by a nitrogen adsorption method and a mercury intrusion method were carried out. In addition, the microstructure of the sample was observed by a SEM.

Comparative Example 1

In Example 1, a sample not subjected to coating treatment using cerium was prepared, and the catalyst performance evaluation test was performed.

Example 2

In Example 1, the reduction treatment of the composite oxide and the formation of the oxide layer were performed in the reverse order, that is, impregnation and coating treatment with cerium nitrate was performed before the reduction treatment at 1000° C., the resultant product was subjected to heat treatment at 500° C., and then reduction treatment was performed at 1000° C. for 10 minutes. The catalyst performance evaluation test using the obtained sample was performed. In the case of preparation in this order, the covered $CeO_2$ layer was reacted with $Al_2O_3$ as the base material at the time of reduction to form $CeAlO_3$.

Example 3

A sample was prepared in the same manner as Example 1, except that $\gamma$-$Al_2O_3$ spherical particles in which micro pores having a size of several nm were increased in amount and relatively large pores having a size of about 1 μm were also contained were used as the oxide base material, and the catalyst performance evaluation test was performed. As a result of evaluation of the composition of this sample by ICP emission spectrometry, the content of Ni was 16.2% by mass.

Example 4

A sample was prepared in the same procedures as in Example 1, except that a mixed aqueous solution of cerium nitrate and samarium nitrate ($Sm(NO_3)_3 \cdot 6H_2O$) at a molar ratio of 1:0.2 was used in the formation treatment of the oxide layer.

Example 5

An aqueous solution of zirconium oxynitrate ($ZrO(NO_3)_2 \cdot 2H_2O$) was used for forming the oxide layer, instead of cerium nitrate. Since a phenomenon that Ni of metal was eluted in the aqueous solution of zirconium oxynitrate was observed, Ni precipitated by reduction was subjected to oxidation treatment in advance to form NiO, and then impregnation and coating treatment was performed. A sample was prepared in the same procedures as in Example 1 except the above-described procedures, and the catalyst performance evaluation test was performed.

Example 6

A sample was prepared in the same procedures as in Example 5, except that a mixed aqueous solution of zirconium oxynitrate and samarium nitrate at a molar ratio of 1:0.2 was used for forming the oxide layer, and the catalyst performance evaluation test was performed.

Example 7

A sample was prepared by changing the order of the reduction treatment and the oxide layer formation treatment in Example 5, and the catalyst performance evaluation test was performed.

Example 8

A sample was prepared in the same procedures as in Example 5, except that a mixed aqueous solution of zirconium oxynitrate and cerium nitrate at a molar ratio of 1:1 was used for forming the oxide layer, and the catalyst performance evaluation test was performed.

Example 9

A sample was prepared in the same procedures as in Example 1, except that hydrolysis of tetraethyl orthosilicate (TEOS) and condensation reaction were used for forming the oxide layer, and the catalyst performance evaluation test was performed.

Example 10

A sample was prepared in the same procedures as in Example 1, except that titanium tetraethoxide ($Ti(OCH_2H_5)_4$) was used and hydrolysis and heat treatment were performed for forming the oxide layer, and the catalyst performance evaluation test was performed.

Comparative Example 2

An aqueous solution of nickel nitrate was subjected to vacuum impregnation by using a cylindrically-formed MgO porous body as the oxide base material. After drying, the MgO surface layer portion and the Ni component were reacted with each other by heat treatment at 1200° C. for 2 hours to form a solid-solubilized product of MgO and NiO ($Ni_xMg_{1-x}O$, $0<x<1$). The solid-solubilized product was subjected to reduction treatment at 1000° C. for 10 minutes in a hydrogen atmosphere to obtain a catalyst material having Ni particles on the surface layer portion. The catalyst performance evaluation test on this material was performed.

Example 11

A catalyst material having Ni particles on the surface layer portion of Comparative Example 2 was further immersed in an aqueous solution of cerium nitrate and subjected to vacuum impregnation, and after drying the catalyst material, heat treatment was performed at 500° C. for 1 hour to form a $CeO_2$ layer. The catalyst performance evaluation test on this sample was performed.

Example 12

A sample was prepared in the same procedures as in Example 10, except that zirconium oxynitrate was used in an oxide layer and a $ZrO_2$ layer was formed, and the catalyst performance evaluation test was performed.

Comparative Example 3

An aqueous solution of nickel nitrate was subjected to vacuum impregnation by using a spherically-formed $TiO_2$ porous body having a particle diameter of 2 to 4 mm as the oxide base material. After drying, the $TiO_2$ surface layer portion and Ni component were reacted with each other by heat treatment at 1300° C. for 2 hours to form a $NiTiO_3$ layer. The $NiTiO_3$ layer was subjected to reduction treatment at 800° C. for 10 minutes in a hydrogen atmosphere to obtain a catalyst material having Ni particles on the surface layer portion. The catalyst performance evaluation test on this material was performed.

Example 13

A catalyst material having Ni particles on the surface layer portion of Comparative Example 3 was further immersed in an aqueous solution of cerium nitrate and subjected to vacuum impregnation, and after drying the catalyst material, heat treatment was performed at 500° C. for 1 hour to form a $CeO_2$ layer. The catalyst performance evaluation test on this sample was performed.

Comparative Example 4

An aqueous solution of nickel nitrate was subjected to vacuum impregnation by using a spherically-formed $SiO_2$ porous body having a particle diameter of 2 to 4 mm as the oxide base material. After drying, the $TiO_2$ surface layer portion and Ni component were reacted with each other by heat treatment at 1400° C. for 1 hour to form a $Ni_2TiO_4$ layer. The $Ni_2TiO_4$ layer was subjected to reduction treatment at 1000° C. for 10 minutes in a hydrogen atmosphere to obtain a catalyst material having Ni particles on the surface layer portion. The catalyst performance evaluation test on this material was performed.

Example 14

A catalyst material having Ni particles on the surface layer portion of Comparative Example 4 was further immersed in an aqueous solution of cerium nitrate and subjected to vacuum impregnation, and after drying the catalyst material, heat treatment was performed at 500° C. for 1 hour to form a $CeO_2$ layer. The catalyst performance evaluation test on this sample was performed.

The performance test results of the catalysts of Examples and Comparative Examples are collectively presented in Table 1.

Example 15

In Example 1, after the reductive precipitation treatment of the catalyst, an aqueous solution of cerium nitrate (Ce$(NO_3)_3 \cdot 6H_2O$) and iron nitrate (Fe$(NO_3)_3 \cdot 9H_2O$) were mixed at a molar ratio of 10:1, the mixed solution was subjected to impregnation and dried, and then heat treatment was performed at 500° C. for 1 hour to form a mixed layer of $Fe_2O_3$—$CeO_2$ on the surface of the catalyst. The catalyst performance evaluation test was performed using this sample. $Fe_2O_3$ was reduced in the reduction treatment before the test and the covered layer became the $CeO_2$ layer having Fe fine particles dispersed therein.

Example 16

In Example 1, after the reductive precipitation treatment of the catalyst, an aqueous solution of cerium nitrate (Ce$(NO_3)_3 \cdot 6H_2O$) and cobalt nitrate (Co$(NO_3)_2 \cdot 6H_2O$) were mixed at a molar ratio of 10:1, the mixed solution was subjected to impregnation and dried, and then heat treatment was performed at 500° C. for 1 hour to form a mixed layer of $CoO$—$CeO_2$ on the surface of the catalyst. The catalyst performance evaluation test was performed using this sample. CoO was reduced in the reduction treatment before the test and the covered layer became the $CeO_2$ layer having Co fine particles dispersed therein.

TABLE 1A

| | First metal particles | Second metal particles | Metal supported amount mass % | Oxide base material | Oxide layer |
|---|---|---|---|---|---|
| Comparative Example 1 | Ni | — | 9.4 | $Al_2O_3$ | — |
| Example 1 | Ni | — | 9.4 | $Al_2O_3$ | $CeO_2$ |
| Example 2 | Ni | — | 9.4 | $Al_2O_3$ | $CeO_2$ |
| Example 3 | Ni | — | 16.2 | $Al_2O_3$ | $CeO_2$ |
| Example 4 | Ni | — | 9.4 | $Al_2O_3$ | $CeO_2$—$Sm_2O_3$ |
| Example 5 | Ni | — | 9.4 | $Al_2O_3$ | $ZrO_2$ |
| Example 6 | Ni | — | 9.4 | $Al_2O_3$ | $ZrO_2$—$Sm_2O_3$ |
| Example 7 | Ni | — | 9.4 | $Al_2O_3$ | $ZrO_2$ |
| Example 8 | Ni | — | 9.4 | $Al_2O_3$ | $CeO_2$—$ZrO_2$ |
| Example 9 | Ni | — | 9.4 | $Al_2O_3$ | $SiO_2$ |
| Example 10 | Ni | — | 9.4 | $Al_2O_3$ | $TiO_2$ |
| Comparative Example 2 | Ni | — | 9.4 | MgO | — |
| Example 11 | Ni | — | 9.4 | MgO | $CeO_2$ |
| Example 12 | Ni | — | 9.4 | MgO | $ZrO_2$ |
| Comparative Example 3 | Ni | — | 9.4 | $TiO_2$ | — |
| Example 13 | Ni | — | 9.4 | $TiO_2$ | $CeO_2$ |
| Comparative Example 4 | Ni | — | 9.4 | $SiO_2$ | — |
| Example 14 | Ni | — | 9.4 | $SiO_2$ | $CeO_2$ |
| Example 15 | Ni | Fe | Ni 8.4 Fe 0.8 | $Al_2O_3$ | $CeO_2$ |
| Example 16 | Ni | Co | Ni 8.4 Co 0.8 | $Al_2O_3$ | $CeO_2$ |

TABLE 1B

| | Test temperature | | | |
|---|---|---|---|---|
| | 250° C. | 300° C. | 350° C. | 400° C. |
| Comparative Example 1 | 1.6 | 10.0 | 50.0 | 78.0 |
| Example 1 | 10.8 | 55.9 | 83.5 | 82.9 |
| Example 2 | 3.0 | 23.3 | 65.3 | 80.3 |
| Example 3 | 18.3 | 64.3 | 87.5 | 83.5 |
| Example 4 | 15.4 | 61.5 | 85.1 | 83.3 |

TABLE 1B-continued

| | Test temperature | | | |
|---|---|---|---|---|
| | 250° C. | 300° C. | 350° C. | 400° C. |
| Example 5 | 12.0 | 49.9 | 78.0 | 82.3 |
| Example 6 | 20.0 | 69.8 | 85.0 | 84.7 |
| Example 7 | 9.1 | 44.0 | 79.1 | 82.0 |
| Example 8 | 19.0 | 65.4 | 85.6 | 84.5 |
| Example 9 | 4.1 | 21.5 | 60.8 | 78.4 |
| Example 10 | 5.2 | 44.3 | 76.6 | 80.6 |
| Comparative Example 2 | 0.0 | 6.7 | 28.9 | 61.6 |
| Example 11 | 4.2 | 28.8 | 67.4 | 80.8 |
| Example 12 | 3.5 | 25.5 | 63.6 | 79.6 |
| Comparative Example 3 | 0.0 | 6.8 | 30.8 | 70.0 |
| Example 13 | 5.1 | 33.3 | 73.0 | 81.6 |
| Comparative Example 4 | 0.0 | 6.5 | 28.3 | 60.2 |
| Example 14 | 4.7 | 28.8 | 68.2 | 80.9 |
| Example 15 | 20.2 | 73.0 | 88.2 | 83.5 |
| Example 16 | 13.2 | 61.8 | 83.5 | 83.1 |

As clearly seen from Tables (Table 1A and Table 1B), it was found that the first metal particles and the oxide base material and the oxide layer, which are integrated with the first metal particles, were allowed to simultaneously exist and thus the methane yield was improved.

Particularly, in a case where the oxide layer was formed after reduction treatment, including Example 1, it was found that the covered oxide was formed without a change in composition thereof and methane was generated at a higher yield. In addition, although not shown in Table 1, it was clear that the generation of CO, which was observed in Comparative Example 1, was almost not observed and $CO_2$ was rapidly reduced to $CH_4$.

Further, in the case of the $Al_2O_3$ base material, the crystalline phase was changed from a γ type of low-temperature type to an α type at the stage of forming the $NiAl_2O_4$ layer by sintering. According to this, it was found that the specific area was decreased; however, when pores having a size of about 1 μm were introduced as described in Example 3, the metal component could be impregnated and precipitated in a wider range, and the first metal particles formed in the deep portion could also contribute to reaction so that the activity was further improved.

Figure 4:
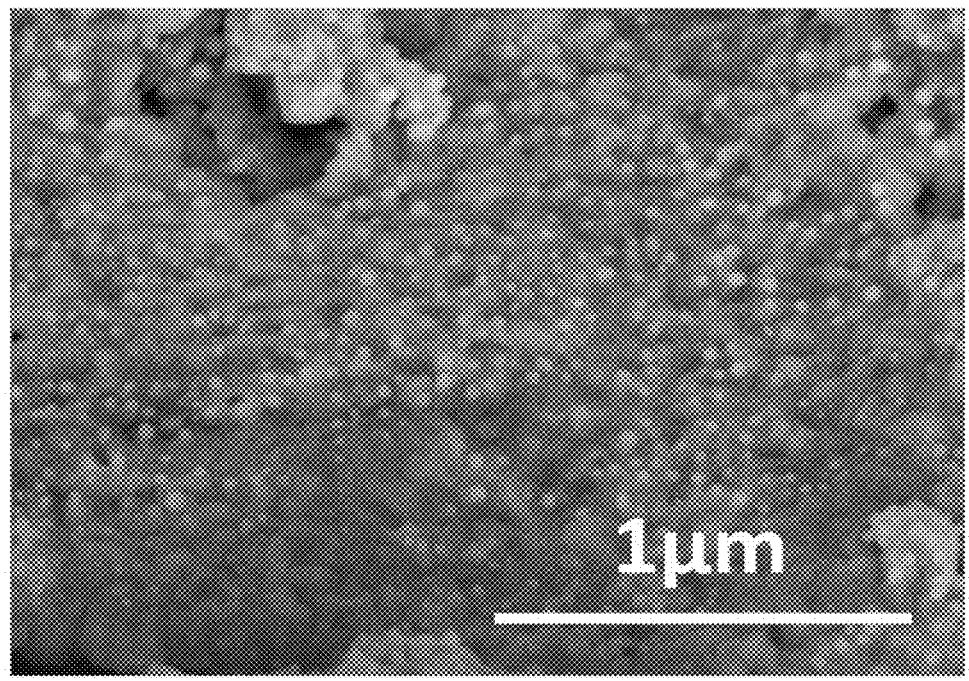
FIG. 4 is a photographed image of the microstructure observation of the catalyst according to the embodiment.

FIG. 4 shows a photographed image of the typical microstructure of the catalyst according to the embodiment. FIG. 4 is obtained by observing the structure of the surface portion of the catalyst prepared in Example 2 and is a reflected electron image photographed in such a manner that an acceleration voltage was set to slightly high and thus the structure of the inner portion of the sample was further captured. In the drawing, particulate white spots are Ni particles of metal. The size of Ni particles was about 30 to 60 nm and was sufficiently larger than the size of Ni particles of a general catalyst. In this way, the Ni particles each independently exist on the surface portion of the catalyst and have a structure in which the particles are highly dispersed. This structure is considered to improve durability. In addition, a Ce-containing layer was formed on the surface portion of this particle and in the vicinity thereof. In this case, $CeO_2$ subjected to coating treatment at the time of reduction treatment was reacted with $Al_2O_3$ of the base material to form a $CeAlO_3$ layer. From a result of catalyst performance test, activity is improved as compared with the case of having no layer. That is, it was found that even when the oxide layer and the oxide base material as described above were reacted with each other to form a compound, there is no problem in improvement of catalyst activity and the effect is achieved.

The sample described in Example 1 in which the oxide layer was formed after the other treatments were performed was also observed with a SEM, but the structure thereof was the same phase as illustrated in FIG. 1B.

Regarding the content of Ni, the test was also performed on a sample having a Ni supported amount of less than 5 wt %, but although there was a $CeO_2$ layer, the catalyst for changing the dissociated $CO_2$ into methane was not sufficient and the performance thereof was deteriorated. In contrast, when the Ni supported amount was increased, the activity was improved, but the activity almost reached to the peak in an area having a Ni supported amount of more than 25% by mass. When the supported amount increases, there is a concern of deterioration in performance caused by combining or growth of Ni particles while in use. For this reason, the supported amount of the first metal particles is preferably set to 25% by mass or less. Further, regarding the oxide layer, in addition to $CeO_2$, the same effect was also recognized in $SiO_2$, $TiO_2$, and $ZrO_2$.

Furthermore, the catalyst performance test was performed on a sample in which a component such as Co, Fe, or Cu was added in advance instead of Ni and the component was precipitated by reduction at the same time of precipitation of Ni. As a result of the test, in all cases, the methane yield was lowered as compared with a case where Ni was added alone. In addition, remaining CO, which is generated when $CO_2$ is not completely turned into $CH_4$, was observed. In contrast, in the catalysts using Co particles or Fe particles together with Ni particles as the first metal particles, the methane yield is improved. When the oxide layer such as $CeO_2$ was provided in the catalysts, it was confirmed that the catalyst activity is improved.

The performance evaluation results of the catalysts in which Fe and Co were added as the second metal particles (Example 15 and Example 16) are presented in Table 1. The methane yield at the low temperature region is improved as compared with the case of using only the first metal particles. On the other hand, in another test, the system in which Fe and Co are simply supported on $Al_2O_3$ did almost not exhibit the catalyst activity. The reason for this is found that this catalyst activity is a specific phenomenon occurring when the second metal particles are combined with the first metal particles. It is considered that fine particles of Fe and Co play a role of assisting the catalyst performance of Ni, that is, act as a cocatalyst.

It was confirmed that the catalysts of Examples are excellent in activity at low temperature without use of a noble metal in a catalytic metal (metal particles). In addition, since the metal particles are configured to be held by both the base material and the oxide layer, the metal particles are less likely to drop off even in high-temperature environment or long-term use. For this point of view, the catalysts of Examples (embodiments) are catalysts that are excellent in terms of all aspects of inexpensiveness, high low-temperature activity, and durability, which are required for practical use. In addition, although methane is generated using the catalyst in Examples, similarly, methanol is generated by changing a raw material from carbon dioxide to carbon monoxide. Further, these catalysts are expected to exhibit higher performance even under increased pressure generally used for increasing the reaction rate.

In the specification, some elements are described only by chemical symbols.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A fuel synthesis catalyst for hydrogenating a gas containing at least one selected from the group consisting of; carbon dioxide and carbon monoxide, the catalyst comprising:
    an oxide base material containing at least one oxide selected from the group consisting of; $Al_2O_3$, MgO, $TiO_2$, and $SiO_2$;
    first metal particles containing at least one metal selected from the group consisting of; Ni, Co, Fe, and Cu and brought into contact with the oxide base material; and
    a porous oxide layer containing at least one selected from the group consisting of; $CeO_2$, $ZrO_2$, $TiO_2$, and $SiO_2$ and having an interface with each of the first metal particles and the oxide base material.

2. The catalyst according to claim 1, wherein the oxide layer partially or entirely covers the oxide base material with which the first metal particles are brought into contact.

3. The catalyst according to claim 1, wherein a content of the first metal particles is 5% by mass or more and 40% by mass or less.

4. The catalyst according to claim 1, wherein an average particle diameter of the first metal particles is 2 nm or more and 200 nm or less, and
    an average particle diameter of the catalyst is 2 mm or more and 10 mm or less.

5. A fuel synthesis catalyst for hydrogenating a gas containing at least one selected from the group consisting of; carbon dioxide and carbon monoxide, the catalyst comprising:
    an oxide base material containing at least one oxide selected from the group consisting of; $Al_2O_3$, MgO, $TiO_2$, and $SiO_2$;
    first metal particles containing at least one metal selected from the group consisting of; Ni, Co, Fe, and Cu and brought into contact with the oxide base material;
    a porous oxide layer containing at least one selected from the group consisting of; $CeO_2$, $ZrO_2$, $TiO_2$, and $SiO_2$ and having an interface with each of the first metal particles and the oxide base material; and
    second metal particles contained in the oxide layer.

6. The catalyst according to claim 5, wherein a main component of the second metal particles is at least one metal selected from the group consisting of; Fe and Co.

7. The catalyst according to claim 5, wherein a proportion of the first metal particles and the second metal panicles contained in the entire catalyst is 5% by mass or more and 40% by mass or less.

8. The catalyst according to claim 5, wherein the oxide layer partially or entirely covers the oxide base material with which the first metal particles are brought into contact.

9. The catalyst according to claim 5, wherein an average particle diameter of the first metal particles is 2 nm or more and 200 nm or less, and
    an average particle diameter of the catalyst is 2 mm or more and 10 mm or less.

10. The catalyst according to claim 1, being a hydrocarbon fuel synthesis catalyst.

11. The catalyst according to claim 1, being an alcohol fuel synthesis catalyst.

12. A fuel synthesis system comprising:
    a reaction column provided with the fuel synthesis catalyst according to claim 1;
    a first raw material supply line supplying one or both of carbon dioxide and carbon monoxide to the reaction column;
    a second raw material supply line supplying hydrogen to the reaction column; and
    a recovery unit recovering a fuel generated by reacting one or both of the carbon dioxide and the carbon monoxide with the hydrogen using the catalyst in the reaction column.

13. The system according to claim 12, wherein a temperature of reaction of the carbon dioxide or carbon monoxide with the hydrogen using the catalyst is 250° C. or higher but 400° C. or lower.

14. The system according to claim 12, wherein a temperature of reaction of the carbon dioxide or carbon monoxide with the hydrogen using the catalyst is 300° C. or higher but 350° C. or lower.

15. The catalyst according to claim 5, being a hydrocarbon fuel synthesis catalyst.

16. The catalyst according to claim 5, being an alcohol fuel synthesis catalyst.

* * * * *